(12) United States Patent
Azizian (10) Patent No.: US 10,271,789 B2
(45) Date of Patent: Apr. 30, 2019

(54) MEASUREMENT AND CONTROL OF BODY FAT PERCENT DURING PREGNANCY

(71) Applicant: NIR TECHNOLOGIES INC., Oakville (CA)

(72) Inventor: Hormoz Azizian, Oakville (CA)

(73) Assignee: NIR Technologies Inc., Oakville, ON (CA)

( * ) Notice: Subject to any disclaimer, the term of this patent is extended or adjusted under 35 U.S.C. 154(b) by 227 days.

(21) Appl. No.: 15/117,736

(22) PCT Filed: Feb. 13, 2015

(86) PCT No.: PCT/CA2015/000082
§ 371 (c)(1),
(2) Date: Aug. 10, 2016

(87) PCT Pub. No.: WO2015/120540
PCT Pub. Date: Aug. 20, 2015

(65) Prior Publication Data
US 2017/0172498 A1  Jun. 22, 2017

Related U.S. Application Data

(60) Provisional application No. 61/940,125, filed on Feb. 14, 2014.

(51) Int. Cl.
*A61B 5/00* (2006.01)
*G06F 19/00* (2018.01)

(52) U.S. Cl.
CPC .......... *A61B 5/4872* (2013.01); *A61B 5/0075* (2013.01); *A61B 5/4343* (2013.01);
(Continued)

(58) Field of Classification Search
CPC .................... A61B 5/4872; A61B 5/4343
See application file for complete search history.

(56) References Cited

U.S. PATENT DOCUMENTS

| 7,039,458 B2 | 5/2006 | Ueda et al. | |
| 7,711,411 B2* | 5/2010 | Azizian | A61B 5/0059 250/339.02 |
| 2003/0023186 A1* | 1/2003 | Ueda | A61B 5/0537 600/547 |

OTHER PUBLICATIONS

International Search Report in PCT/CA2015/000082 dated May 11, 2015.

(Continued)

*Primary Examiner* — Eric D. Bertram
(74) *Attorney, Agent, or Firm* — Manelli Selter PLLC; Edward J. Stemberger (57) ABSTRACT

The present invention provides a method for measuring the body fat percent and fat accretion during pregnancy, which preferably utilizes a Fourier transform near infrared spectroscopy (FT-NIR) fat determination method. The FT-NIR results can be used to measure and monitor body fat percent, and used to measure the mother's fat accretion rate. A method to monitor weight gain in a pregnant subject is provided wherein the body fat percentage of the subject is maintained at a constant level during gestation, and the subject's fat accretion rate is monitored so as to follow the fat accretion rate provided by using pre-defined fat accretion determination formulae. By measurement of the body fat percent and fat accretion rates, the weight gain of a subject can be monitored and/or controlled during pregnancy.

7 Claims, 3 Drawing Sheets

(52) U.S. Cl.
CPC ............ *A61B 5/486* (2013.01); *A61B 5/7225* (2013.01); *A61B 5/7257* (2013.01); *G06F 19/00* (2013.01); *G06F 19/3475* (2013.01); *A61B 2503/02* (2013.01); *A61B 2576/00* (2013.01)

(56) References Cited

OTHER PUBLICATIONS

International Preliminary Report on Patentability in PCT/CA2015/000082 dated Aug. 16, 2016.
Azizia et al., "First Direct Body Fat Content Measurement During Pregnancy Using Fourier Transform Near-Infrared Spectroscopy", Applied Spectroscopy, vol. 68, Issue 3, pp. 379-382, Feb. 24, 2014.
Sohlstrom et al., "Changes in total body fat during the human reproductive cycle as assessed by magnetic resonance imaging, body water dilution, and skinfold thickness: a comparison of methods", American Journal of Clinical Nutrition, vol. 66, Issue 6, pp. 1315-1322, Jan. 1998.
Josse, et al., "Body fat content determination in premenopausal, overweight, and obese young women using DXA and FT-NIR", Obesity, vol., 19, Issue 7, pp. 1497-1502, Mar. 2011.

\* cited by examiner

MEASUREMENT AND CONTROL OF BODY FAT PERCENT DURING PREGNANCY

FIELD OF THE INVENTION

The present invention relates to the field of the measurement and control of body fat percentage and body fat accretion, and in particular, relates to a method for the measurement and control of body fat percentages and body fat accretion, during pregnancy.

BACKGROUND OF THE INVENTION

Energy requirement during pregnancy is important to ensure the safe delivery of healthy offspring. It is well established that protein and fat deposition occurs in baby and maternal tissues during pregnancy. However, there are no direct and reliable methods available to measure body composition during pregnancy in order to manage and monitor the energy requirements of pregnant women. The World Health Organization (WHO) has calculated the mean fat accretion which occurs during pregnancy, in the period of up to 36 weeks from gestation, using mainly pre and post pregnancy measurements (*Chapter 6—Energy Requirements of Pregnancy, Human Energy Requirements: Report of a Joint FAO/WHO/UNU Expert Consultation Rome*, 17-24 Oct. 2001, pp 53-62.). However, this approach suffers from large estimation errors and it is not based on actual measurements taken during the pregnancy.

It is also known that both magnetic resonance imaging (MRI) and dual-energy X-ray absorptiometry (DXA) are considered accurate methods to determine body fat percent in a human subject. However, these approaches are contraindicated during pregnancy because of the health concerns with exposure to a magnetic field or x-rays, respectively.

On the other hand, other known non-invasive or minimally invasive methods such as skin fold or bioimpedence measurements, have not been found to be reliable. Other known methods for determining body fat percent are also not generally desirable for use on pregnant women. These include underwater weighing, air displacement plethysmography, body water dilution technique, and the like. Other approaches to determining body fat percentages, including such as body mass index (BMI), are also typically not appropriate due to inherent inaccuracies.

In U.S. Pat. No. 7,711,411, the contents of which are incorporated herewith, a non-invasive technique to measure body fat percent is described which utilized a Fourier transform near infrared spectroscopy (FT-NIR) technique. The FT-NIR technique is relatively quick and easily conducted, and involves minimal intrusion. In a preferred approach, a fiber optic probe is directed at the back of a subject's ear and then the reflected or transmitted FT-NIR signals are processed, using pre-developed calibration models, to provide the subcutaneous fat percentages of an individual, in minutes. More importantly, the measurements from the FT-NIR technique were found to equate well to other, more traditional tests for body fat percent such as DXA and MRI.

In U.S. Pat. No. 7,039,458, a technique is described for measuring and controlling body fat percent during pregnancy, but this technique relies on the use of bioelectrical impedance. In addition, the described technique requires the user to determine and input various parameters directly into the system, including non-related factor (e.g. the baby's weight) using various other techniques.

Health Canada has published guidelines for weight gain during pregnancy based on the mother's initial BMI ("The Sensible Guide to a Healthy Pregnancy"; Government of Canada, Health Canada, 2008—Revised 2012). These are reproduced below:

| BMI | Recommended Weight Gain |
| --- | --- |
| Below 18.5 | 12.5 to 18 kg (28 to 40 pounds) |
| Between 18.5 and 24-9 | 11.5 to 16 kg (25 to 35 pounds) |
| Between 25.0 and 29.9 | 7 to 11.5 kg (15 to 25 pounds) |
| 30 and more | 5 to 9 kg (11 to 20 pounds) |

However, these values only provide a guideline for total weight gain during the 9 month pregnancy, and do not describe or advise of any details of the timing of the expected weight gain. Moreover, at the low BMI, and in particular, the high BMI values, the timing of fat accretion can be critical.

It would therefore be desirable to provide a technique for measurement of body fat percent during pregnancy, and thereafter use those measurements to control body fat percent and fat accretion during pregnancy.

It would therefore also be desirable to provide a method for monitoring body fat percent and fat accretion during pregnancy.

Further, it would also be desirable to measure, monitor and control the weight gain of the user, during the various stages of pregnancy, while ensuring the health of the mother and baby by monitoring fat accretion.

These and other advantages, as set out hereinabove, as well as other objects and goals inherent thereto, are at least partially or fully provided by the body fat percent measurement technique of the present invention, particularly when used in conjunction with fat gained, and weight gain measurements, as set out herein below.

SUMMARY OF THE INVENTION

It is a principal advantage of the present invention to provide a technique for the determination of body fat percent during pregnancy. It is a further advantage of the present invention to provide a method for use of the body fat percent measuring technique to track, and otherwise monitor, the body fat percent of the user, during pregnancy.

It is a still further advantage of the present invention to monitor the mass of fat gained, and the rate of fat gain, during the various stages of the pregnancy, in order to monitor and control the total weight gained during pregnancy. Control of these aspects, ensures that the level of fat gain and/or weight gain at any time period during pregnancy is appropriate for that stage of the pregnancy.

It is yet still a further advantage of the present invention to provide a method to modify and/or control the body fat percent and the fat gained by the user, during pregnancy, in order to maintain the body fat percent and weight gain of the user, within suggested guidelines, during the course of the pregnancy.

The advantages set out hereinabove, as well as other objects and goals inherent thereto, are at least partially or fully provided by the body fat percent measurement technique and system of the present invention, as set out herein below.

Accordingly, in one aspect, the present invention provides a method for determining the body fat percent during pregnancy, preferably using an FT-NIR technique, and more preferably with an FT-NIR technique which has been calibrated using a calibration model adapted for these applications.

In a further aspect, the present invention also provides a method for determining the appropriate body fat percent during pregnancy by comparing the measured body fat percent of the user, to pre-established guidelines which are established for the user.

In a still further aspect, the present invention also provides a method to control body fat percent during pregnancy by comparing the measured body fat percent during pregnancy, comparing the measured body fat percent to the pre-established guidelines, and adjustment of the user's diet should the measured body fat percent fall outside of the pre-established guidelines.

In a yet still further aspect, the present invention also provides a method to monitor, control and adjust fat gained during pregnancy by measuring the fat gain rate for various stages of pregnancy, and adjusting the fat gain rate, when necessary, in conjunction with the body fat percent measurement, to adjust and modify the fat gain rate and body fat percent of the user. This approach is preferably conducted in such a manner that the fat gain rate is controlled during at least three stages of pregnancy, as set out hereinbelow.

Accordingly, the present invention provides a method for the measurement and control of body fat percent and body fat accretion during pregnancy comprising:

measuring the body fat percent of a mammal at the beginning of said pregnancy, and monitoring the body fat percent of said mammal during the course of said pregnancy;

measuring the body fat mass of a mammal at the beginning of said pregnancy, and monitoring the body fat mass of said mammal during the course of said pregnancy;

pre-establishing guidelines for the body fat mass gain for a plurality of periods for said pregnancy; and adjustment of the diet of said mammal during said pregnancy to: (i) ensure that the body fat percentage of said mammal remains essentially constant during the course of said pregnancy; and (ii) ensure that the body fat mass gain of said mammal is within the pre-established guidelines for body fat mass gain, for each period of said pregnancy.

Preferably, the mammal is a human female, and the plurality of time periods, are weeks.

In a still yet further aspect, the present invention also provides an apparatus for measuring and monitoring body fat percent, and/or fat accretion in a female subject, by measuring body fat percent of said subject on a regular basis, wherein said apparatus preferably comprises an FT-NIR measurement apparatus for measurement of the body fat percentage and body fat mass, and which includes computerized means for calculating body fat percent and fat mass of the subject, by using a pre-determined calibration model or matrix. Preferably, the apparatus additionally comprises a database of the data collected for each user, and this data is preferably stored on a computerized storage device. Preferably, only a single computerized device is required for collection and storage of the results of the body fat percentage and fat mass determinations, so as to compare the body fat percentages to previously measured values, and to determine the fat accretion rate of the subject, and to compare the determined fat accretion rate to at least one pre-defined fat accretion formula.

As such, the present invention preferably also provides an apparatus for measurement and control of body fat percentage and body fat accretion of a mammal during pregnancy comprising:

means for measurement of the body fat percentage of said mammal at the beginning of said pregnancy, and throughout said pregnancy;

means for measurement of the body fat mass of said mammal at the beginning of said pregnancy, and throughout said pregnancy;

a database to record the body fat percentage and body fat mass data collected for said mammal during the course of said pregnancy;

a calculation device for determining pre-established guidelines for the body fat percentage and body fat mass during the course of said pregnancy; and notification means to alert said mammal that their diet requires modification, if the body fat percentage or body fat mass is outside of said pre-established guidelines.

The means for measuring the body fat percentage and body fat mass of the mammal, can be accomplished using any suitable prior art body fat measurement device. Preferably, the means is an FT-NIR device which has been suitably calibrated using a suitable matrix.

Storage of the observed data is preferably accomplished using any suitable computerized device, as is the calculation of the pre-established guideline for body fat percentage and body fat mass. However, these could also be calculated by hand, or merely charted on a suitable graph.

Notification to the mammal could be provided by a computer output, but might also simply be advice from the user's doctor, or the like.

DETAILED DESCRIPTION OF THE INVENTION

In the present application, the term "body fat percent" refers to the body fat percent of the pregnant woman. While any suitable technique might be used that can provide the requisite accuracy, the body fat percent of a pregnant user is most easily, and therefore most preferably measured, using an FT-NIR technique. The FT-NIR technique is preferably one based on a calibration model or matrix that has been developed for use on human subjects, as is described in U.S. Pat. No. 7,711,411.

From the FT-NIR data, the actual amount of fat mass gained by the user can also be measured and determined, so that the fat mass gain, and the fat mass gain rate, can also be monitored.

The weight gain rate of the user is easily measured and monitored, as an optional part of the present invention, by using traditional scales, and the like, in order to determine the users weight at any given time.

It is to be noted that the present invention provides a technique where preferably the body fat percent of the user is monitored and controlled, and the amount of fat gained is also monitored and controlled. By controlling these aspects, the user can be assured that the weight gain encountered at any time during pregnancy will be appropriate to the development of a healthy baby, while ensuring that the mother has sufficient fat to meet her energy requirements.

However, by following the recommended body fat percentages, and the appropriate weight gain rate, fat accretion in the mother is preferably done in a manner wherein excess fat gain is avoided. As a consequence, the mother's weight gain during pregnancy can be controlled. As a result, the present invention provides a method to ensure that insufficient, and more typically, excess weight gain is avoided.

With this technique the user's weight at the end of the pregnancy should not be excessive, or deficient, but will provide an appropriate weight gain for the gestation period.

The technique of the present invention is of most use to those women who have a typical healthy, pre-pregnancy weight of between 45 and 100 kg, and preferably having a body fat percent of between 12 to 45%. While the results from the present invention can be utilized to monitor and control women outside of these weight and body fat limitations (such as anorexic, or obese women), the techniques should be used with caution outside of the suggested preferred values. For example, malnourished or obese women may require additional monitoring and adjustment of the present technique, in order to address their individual health requirements.

However, regardless of the users weight or fat content, the technique of the present invention can still be used to provide valuable insight into the weight gain of the pregnant user.

Most preferably, the pre-pregnancy weight of the woman is between 55 and 75 kg, and the pre-pregnancy body fat percent is between 15 and 40%, and more preferably between 20 and 35%.

It is also expected that the pre-pregnancy weight of the women will be available in order to determine the weight gain, and the weight gain rate, the fat mass gain, and the fat mass accretion rate, during the entire pregnancy. However, this is not necessarily required.

Additionally, knowledge of the pre-pregnancy body fat percentage would be advantageous, but again, is not required Collection of the user's data on fat gain, fat gain rate, and body fat percent can be initiated at any time during the pregnancy period, but preferably is initiated within the first trimester.

It is also expected that the total weight gain during gestation will preferably be between 8 and 20 kg, for most women, with the most preferred weight gain being between 10 and 14 kg, as suggested by WHO (ibid), for most individuals.

The fat gain rate during gestation can be monitored, to be used in conjunction with body fat percentage observations. The body fat percent (and the fat gained) can be controlled by adjustment of the individual's caloric intake so that both values are controlled with the desired range, for the gestation term. Normally, the gestation term can be broken down in at least three stages (e.g. the first, second and third trimesters) and the fat gain rate and body fat percent can be monitored during each of the at least three stages.

By control of the fat gained, the fat gain rate, and the total weight gain during pregnancy, the post-partum weight loss, and the return to pre-pregnancy weight and body fat percent, can be facilitated. Moreover, by monitoring the body fat percent, and the fat gain rate, in accordance with the present invention, the system provides a method to ensure that the weight gained during the pregnancy period, is appropriate for a healthy mother and infant.

It will also be noted that the technique and systems of the present invention are of most use in controlling the body fat percent and fat gain of a pregnant human female, but the techniques and systems of the present invention are equally applicable to non-human female mammals.

In the practise of the present invention, the body fat percentage of a user during pregnancy is measured, and preferably measured using an FT-NIR technique. Based on experimental evidence, it has been somewhat surprisingly found that the body fat percent of the user should remain essentially constant over the gestation period. Despite the weight gain of the mother, and the change in growth rate of the baby during the three trimesters of pregnancy, it was found that the body fat percent of the mother is preferably maintained constant, and preferably stays essentially the same as the body fat percent of the mother, prior to pregnancy. As such, during the entire term of the pregnancy, the body fat percentage of the mother should remain constant.

In the context of the present invention, by stating that the body fat percentage remains constant, it is meant that the body fat percent of the user should not vary by more than 10%, and more preferably, by less than 5%, of the user's pre-pregnancy body fat percent. Most preferably, the body fat percent of the user will not vary by more than 2% of the user's pre-pregnancy body fat percent.

In the situation where the pre-pregnancy body fat percent measurement is not available, the body fat percent is preferably held constant at the same body fat percent of the initial body fat percent measurement for that user.

As such, the body fat percent of the user is preferably monitored by being measured at regular intervals during pregnancy. Should the users body fat percentage begin to increase or decrease, the caloric intake of the user can be reviewed and adjusted, as and when necessary.

In addition, data on the fat gained by the pregnant mother is also preferably collected on a regular basis. For a human female, the fat gained can be monitored and compared to a suggested calculated fat gained value. The calculated fat gained value depends on the time since inception. Moreover, the rate at which fat is gained, varies during the three trimesters of the pregnancy. The rate of fat accretion is preferably calculated using a series of formulas to estimate the mothers fat gained during each trimester.

In a preferred aspect, the fat gained by the user during the first trimester (i.e. weeks 1 to 13) is preferably calculated by Formula I, $$Y = \alpha X \quad (I)$$

wherein Y is the fat gain in kg, X is the number of weeks since inception, and $\alpha$ is between 0.08 to 0.16, and more preferably, between 0.12 and 0.14. As such, the fat gained in the first trimester is preferably between about 0.12 to 0.14 kg per week.

The fat gained by the user during the second trimester (i.e. weeks 14 to 26) is preferably calculated by Formula II, $$Y = \beta(X-13) \quad (II)$$

wherein Y and X are as previously defined, and $\beta$ is between 0.25 and 0.42, and more preferably, between 0.31 and 0.36. As such, the fat gained in the second trimester is preferably between about 0.31 to 0.36 kg per week.

The fat gained by the user during the third trimester (i.e. weeks 27 to 39) is preferably calculated by Formula III, $$Y = \gamma(X-26) \quad (III).$$

wherein Y and X are as previously defined, and $\gamma$ is between −0.1 and 0.2, and more preferably, between 0.08 and 0.16. As such, the fat gained in the third trimester is preferably between about 0.08 to 0.16 kg per week.

For a human female, it is assumed that the total number of weeks of pregnancy is approximately 39, with each trimester being 13 weeks.

It should again be emphasised that the body fat percentage of the mother is expected to remain essentially constant during the 39 weeks of pregnancy, and as such, the ratio of fat to non-fat weight gain should be controlled to comply with formulae I, II and III.

The formulae presented herein provide a general guideline for fat accretion during pregnancy, for a variety of females. However, the formulae provided can also be refined to account for other variables, including the mothers age, initial weight, size, ethnicity, residence, or the like. Other values for α, β and γ can be used depending on how closely the fat gain is to be monitored.

Preferably, the user's fat gain remains within 10% of the calculated value, and more preferably, within 5% of the calculated user's fat gain. Most preferably, the user's fat gain is preferably maintained with 2.5% of the calculated fat gain value.

Again, should the fat gained value vary from the calculated values, the caloric intake of the user can be adjusted, as necessary, to maintain the user's body fat percent and fat gained at or near the values suggested by the present invention.

Therefore, in a most preferred embodiment of the present invention, both the body fat percent and the fat gained values are monitored during gestation, with the aim of holding the mother's body fat percent essentially constant, and the fat gained amount being maintained at levels in accordance with Formulas I, II and III.

It will be noted that although the body fat percent of the user preferably remains constant, with the increase in weight normally resulting from pregnancy, the absolute amount of fat in the mother will increase during the term of the pregnancy. By following the practise of the present invention, the mother will have sufficient fat content to facilitate the development of a healthy infant while ensuring that the mother remains well nourished during pregnancy. This can be achieved without the accretion of undesirably high, or low, fat amounts, which can lead to undesirably high, or low, weight gain.

BRIEF DESCRIPTION OF THE DRAWINGS

Embodiments of this invention will now be described by way of example only in association with the accompanying drawings in which:

FIG. 1 is the FT-NIR absorption spectra for two subjects with 29% (subject 1) and 44% (subject 2) body fat percent in FIG. 1A. The first derivative of the expanded region from 5500 to 6100 $cm^{-1}$ of the absorption spectra for the two subjects, is shown in FIG. 1B;

DETAILED DESCRIPTION OF THE PREFERRED EMBODIMENTS

The novel features which are believed to be characteristic of the present invention, as to its structure, organization, use and method of operation, together with further objectives and advantages thereof, will be better understood from the following discussion, and by use of examples describing experimental results. It is expressly understood, however, that the results are presented for the purpose of illustration and description only and are not necessarily intended as a definition of the limits of the invention.

Also, unless otherwise specifically noted, all of the features described herein may be combined with any of the above aspects, in any combination.

Materials and Methods

All spectra were obtained using a Bruker Optics (Billerica, Mass., USA) FT-NIR spectrometer, model Matrix F, equipped with a diffuse reflection fiber optic probe, and using a proprietary software from instrument supplier (OPUS). The FT-NIR spectrometer was equipped with a thermoelectrically cooled InGaAs detector. Data were collected at 8 $cm^{-1}$ resolution using the Blackman-Harris 3-term apodization function at room temperature.

During the FT-NIR measurement, the fiber optic probe was placed on the back of the ear, upper part, and absorption spectra were collected. Five replicate absorption spectra were measured each time. This was repeated 2 or 3 times following a visual inspection of the absorption spectra for any light scattering due to imperfections of the ear cartilage.

Previous experience had shown that ear piercing caused irregularities in the cartilage that resulted in greater light scattering and lower reflection of the light beam. This affected the results, since the model is based on the assumption that the scattering coefficient for both the reference and the subject spectra is the same. These spectra were subsequently used to generate an average spectrum. Average spectra collected were processed and analyzed using a pre-developed Partial Least Squares (PLS) calibration model (NIR Technologies, Oakville, Ontario, Canada) for the determination of subcutaneous body fat, in minutes. The OPUS program uses PLS1.

Weight gained was measured by a standard set of weight scales, and the fat gained, was calculated from the collected data.

Results and Discussion

In this experiment, the body fat percent of women during pregnancy was measured using FT-NIR. These measurements are not generally available with reliable MRI or DXA body fat percent measurement techniques due to the health concerns of using these techniques.

Figure 1A:
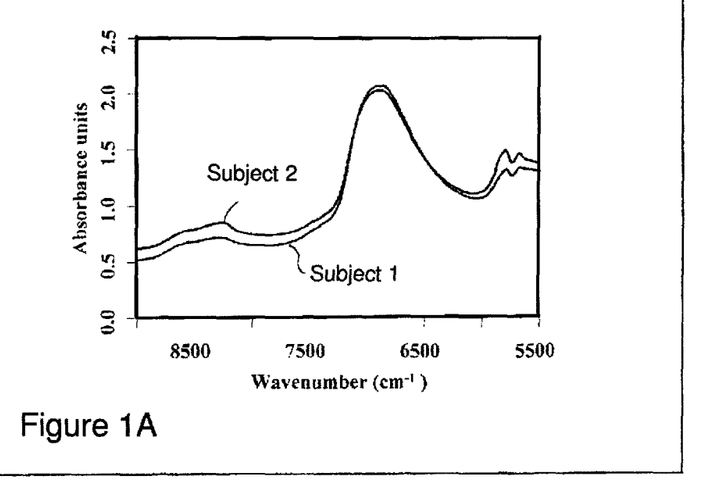
Figure 1B:
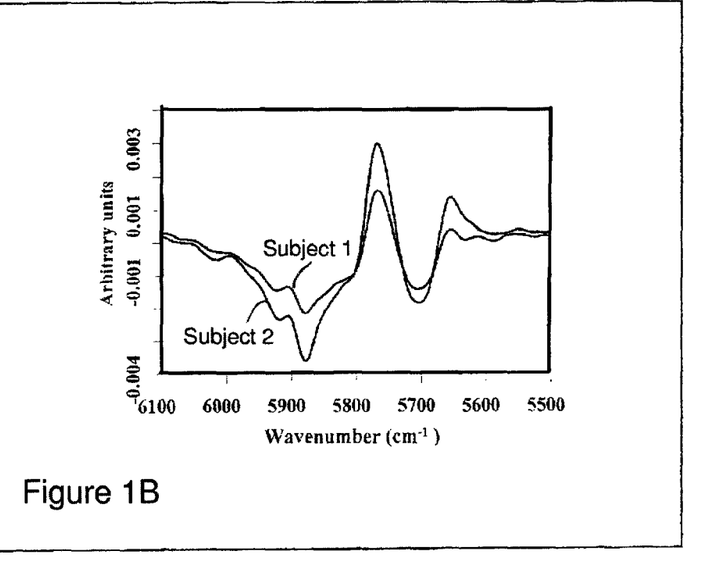

As background, FIGS. 1A and 1B show the FT-NIR absorption and the first derivative spectra of the pregnant subjects with a body fat percent of 29% (subject 1—at 29 weeks) and 44% (subject 2—at 32 weeks), respectively. There are significant differences in the absorption spectrum in the region of first overtone for —CH and —CH2 vibrations between 5500 and 6100 $cm^{-1}$. The first derivative spectrum of this expanded region shows substantial spectral difference for the first subject with 29% and second subject with 44% body fat percent (FIG. 1B).

Table 1 shows data measurements for fat and fat free mass from before pregnancy to 52 wks post partum, for the three test subjects, and the results from a prior art Swedish study showing only the beginning and end fat and fat free mass values (A. Sohlström, E. Forsum E. "*Changes in Total Body Fat During the Human Reproductive Cycle as Assessed by Magnetic Resonance Imaging, Body Water Dilution, and Skinfold Thickness: a Comparison of Methods*". Am. J. Clin. Nutr. 1997. 66(6): 1315-1322.). The average fat mass with the standard deviation for repeat measurements for the three subjects obtained at twenty different occasions throughout the pregnancy was 28.1±0.5 kg body fat.

In Table 2, results related to the amount of fat gained during pregnancy for the same three subjects is shown, together with prior art values from a study conducted by the WHO (ibid). This data shows the WHO level of weight gain was 12.9 kg. It can be noted that while subject 1 of the present study gained a total of 21.9 kg, which is clearly above the WHO recommendation, subject 2 gained less weight for a more moderate increase of only 13.2 kg. Subject 3 gained a total of 18.9 kg, which was again, clearly above the WHO desired value.

As stated above each actual measurement shown in the table, represents an average of five individual spectra taken.

Only two FT-NIR measurements were taken of the first subject during pregnancy, even though many more could have been taken, since the technique poses no health hazards to the mother or fetus. To further investigate the apparent difference in the rate of fat accretion before and after the 29 wk measurement in subject 1, several additional measurements of subject 2 and 3 were taken throughout their pregnancys.

Figure 2:
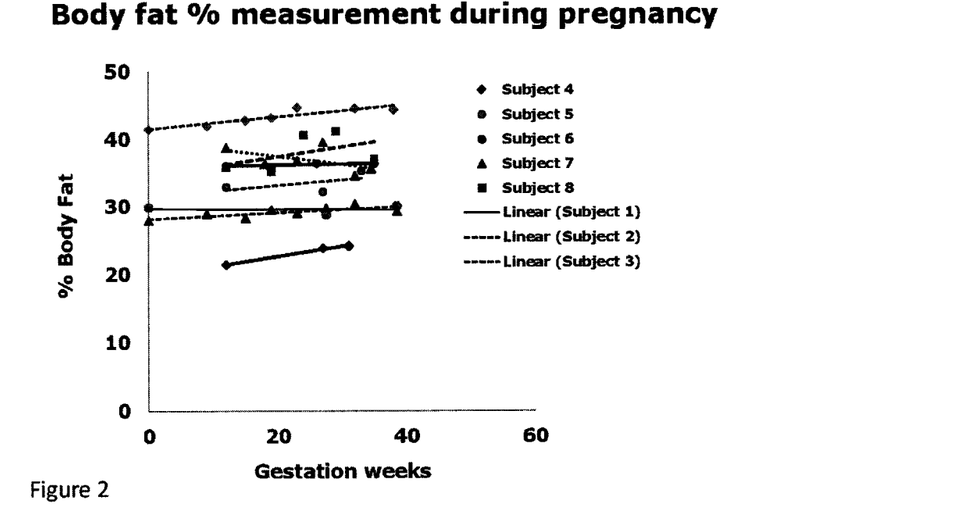
FIG. 2 is a graph of body fat percent during pregnancy for various subjects, as determined by FT-NIR.

The body fat percent results for the three subjects of the present study, are shown in FIG. 2 and these results show that the body fat percent remains essentially constant (±5%) during the entire pregnancy.

Values from several other test subjects (Nos. 4 to 8) are also included in the graph, showing that body fat percentage for virtually all subjects remained essentially constant.

Figure 3:
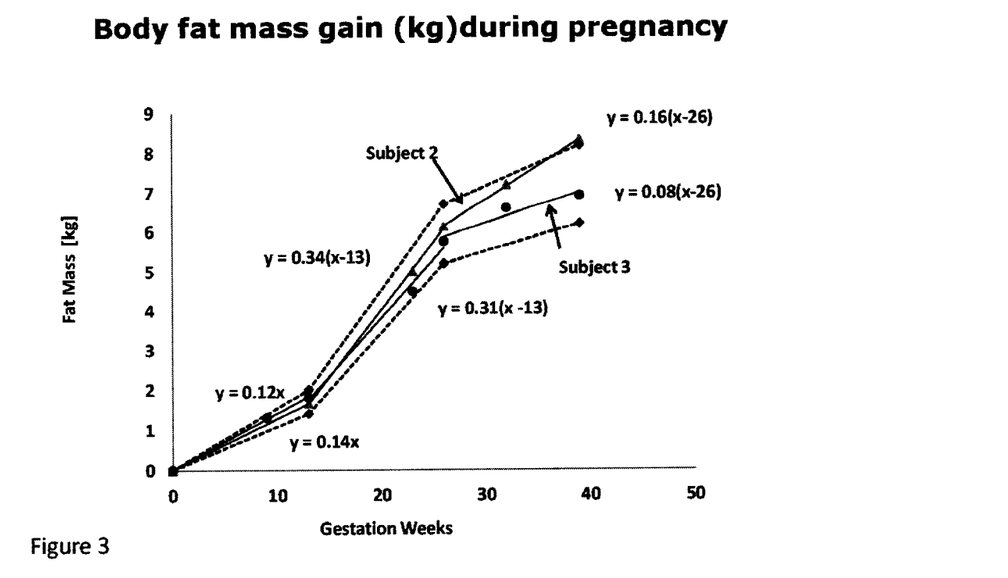
FIG. 3 is a graph of the fat mass accretion for two subjects, during gestation as determined by FT-NIR spectroscopy.

From the more detailed information from subjects 2 and 3, the fat gained during gestation is shown in FIG. 3, and it can be seen that fat mass gained, or fat mass accretion, for the mother, follows an S curve. In particular, it can be seen that the fat mass accretion was moderate in the first trimester, increased significantly in the second trimester, and levelled off during the third trimester. Suggested body fat mass gain lines for each trimester, are also shown as dashed lines, to indicate a selected range of body fat mass gain. Maintaining body fat mass gain between these lines would be beneficial, although keeping the body fat mass gain towards the lower line, would be preferred.

In FIG. 3, the lower dashed line has α, β and γ values of 0.11, 0.29 and 0.07 respectively. The upper dashed line has α, β and γ values of 0.15, 0.36 and 0.12 respectively.

It can be noted that in trimester 3, subject 2's fat mass increased to a level above the suggested upper level. As such, she would have likely has been advised to better control this fat gain, and adjust her diet accordingly.

The benefit of the present invention is that using the FT-NIR technique, these measurements could be made directly in minutes to provide accurate and individualized support throughout the pregnancy.

Figure 4:
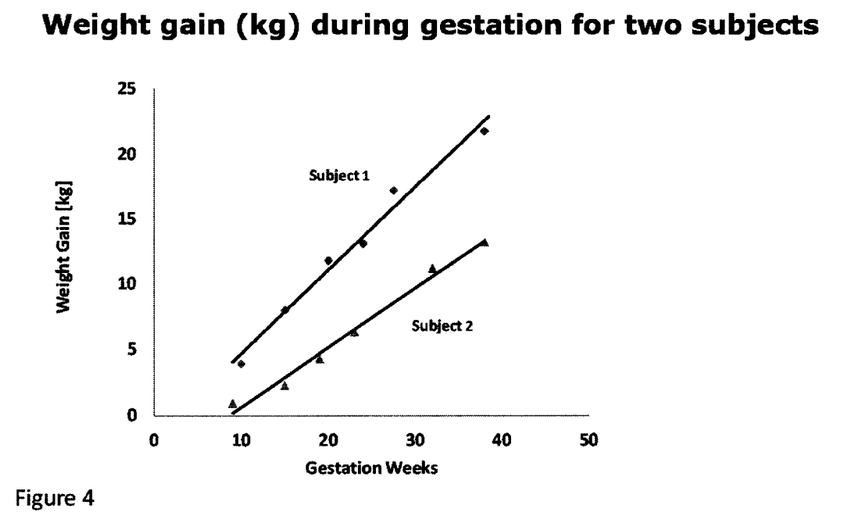
FIG. 4 is a graph of the weight gain during pregnancy for two subjects.

In FIG. 4, the weight gain for two subjects, as taken from Table 1, is shown. The total weight gain during pregnancy can vary from the mother's fat mass gain depending on other factors, including for example, the rate of non-fat mass gain, the accumulation of water or amniotic fluid, and the fact that the body fat content of the baby may vary from that of the mother.

From this data, it can be noted that the percent body fat of the subjects in this study remained relatively constant throughout pregnancy at about 29% for subject 1, about 44% for subject 2, and about 29% for subject 3, while the fat and fat free masses both increased for all three subjects (Table 1).

Two weeks after giving birth (baby's birth weight for subject 1, was 3.38 kg, for subject 2, was 3.64 kg, and for subject 3, was 3.53 kg.) there were significant differences in fat mass and changes in percent fat between the three subjects (Table 1). Subjects 1 and 3, but not subject 2, retained much of the fat accumulated during pregnancy, which was also reflected in their respective percent body fat percentages (Table 1). Subjects 1 and 2 lost most of the accumulated weight and all of the accumulated fat in the year following the pregnancy (Table 1). The corresponding data for subject 3 is not available.

The fat gain and weight gain of all of the subjects in this study, up to 38 wks, were generally higher than those reported by the WHO even after extrapolating the 36 wk data to 38 wks (Table 2); subjects 1 and 3, but not 2, were outside the range of 10 to 14 kg, while subject 2 was at the upper edge of this suggested value.

However, the results observed for the three subjects do not appear to show a consistent relationship between the mother's fat gain and the mother's weight gain, as evidenced by the fat gain/weight gain ratio. It might also be noted that subject 2 with a lower weight gain had a slightly higher fat gain (Table 2), which would be opposite to that predicted by a body mass index (BMI) assessment, if that approach to body fat percentage measurement, had been used.

TABLE 1

| Subjects | Pre-Pregnancy | Pregnancy[1] | | | | | | | Postpartum[2] | |
|---|---|---|---|---|---|---|---|---|---|---|
| | | 9 wks | 15 wks | 19 wks | 23 wks | 29 wks | 32 wks | 38 wks | 2 wks | 52 wks |
| Swedish study [5] | | | | | | | | | | |
| Fat mass (kg) | 17.5 | | | | | | | | 21.1 | 19.1 |
| Fat free mass (kg) | 47.1 | | | | | | | | 50.1 | 48.2 |
| Fat (%) | 26.6 | | | | | | | | 29.4 | 27.8 |
| This study subject 1 | | | | | | | | | | |
| Fat mass (kg) | 22.5 | | | | | 26.9 | | 29.3 | 28.2 | 21.7 |
| Fat free mass (kg) | 52.9 | | | | | 66.3 | | 68.1 | 57.9 | 59.2 |
| Fat (%) | 29.9 | | | | | 28.8 | | 30.1 | 32.7 | 26.8 |
| This study subject 2 | | | | | | | | | | |
| Fat mass (kg) | 30.2 | 31.1 | 32.1 | 33.0 | 35.2 | | 37.4 | 38.1 | 30.7 | 27.8 |
| Fat free mass (kg) | 42.5 | 42.6 | 42.9 | 44.0 | 43.8 | | 46.5 | 47.8 | 46.1 | 41.1 |
| Fat (%) | 41.5 | 42.2 | 42.8 | 42.9 | 44.6 | | 44.6 | 44.4 | 40.0 | 40.3 |
| This study subject 3 | | | | | | | | | | |
| Fat mass (kg) | 20.9 | 22 | 23.1 | 24.7 | 25.4 | 26.6 | 27.5 | 27.5 | 25.2 | |
| Fat free mass (kg) | 54.1 | 54.1 | 58.5 | 59.0 | 62.1 | 62.7 | 64 | 66.4 | 59.8 | |
| Fat (%) | 27.9 | 28.9 | 28.3 | 29.5 | 29 | 29.8 | 30.4 | 29.3 | 29.6 | |

[1]No MRI measurements were possible during pregnancy
[2]Postpartum 52 weeks measurement for subject 3 is not available

TABLE 2

| Subjects | 9 wks | 15 wks | 19 wks | 23 wks | 29 wks | 32 wks | 36 wks | 38 wks [1] |
|---|---|---|---|---|---|---|---|---|
| WHO study [1] | | | | | | | | |
| Mean fat gain (kg) | | | | | | | 3.7 | 4.0 |
| Mean weight gain (kg) | | | | | | | 11.9 | 12.9 |
| Fat gained/weight gained | | | | | | | 0.31 | 0.3 |
| This study subject 1 | | | | | | | | |
| Fat gain (kg) | | | | | 4.4 | | | 6.8 |
| Weight gain (kg) | | | | | 17.8 | | | 21.9 |
| Fat gained/weight gained | | | | | 0.25 | | | 0.31 |
| This study subject 2 | | | | | | | | |
| Fat gain (kg) | 0.5 | 1.6 | 2.8 | 5.0 | | 7.2 | | 7.9 |
| Weight gain (kg) | 0.9 | 2.3 | 4.3 | 6.3 | | 11.2 | | 13.2 |
| Fat gained/weight gained | 0.56 | 0.70 | 0.65 | 0.79 | | 0.64 | | 0.60 |
| This study subject 3 | | | | | | | | |
| Fat gain (kg) | 1.1 | 2.2 | 3.8 | 4.5 | 6.5 | 7.1 | 6.8 | 6.6 |
| Weight gain (kg) | 1.2 | 6.6 | 8.7 | 12.5 | 14.3 | 17 | 18.3 | 18.9 |
| Fat gained/weight gained | 0.96 | 0.33 | 0.44 | 0.36 | 0.45 | 0.42 | 0.37 | 0.35 |

[1] Extrapolated data from the WHO report from 36 to 38 wks

From this assessment, it can also be noted that subjects 1 and 3 could have been encouraged during their pregnancy to reduce their caloric intake, in order to reduce weight gain during gestation, while maintaining healthy fat mass gain.

Additionally, it can be noted that the current FT-NIR measurements before and after pregnancy can be compared to the Swedish study (Table 1) in which pre and post pregnancy body fat changes were determined using MRI. Even though the fat measurements of the subjects in the current study were slightly higher than the mean values reported in the Swedish study, they were within the observed variation.

As such, it is submitted that the present invention is the first report of a direct and accurate determination of the body fat percent of women during pregnancy. The determination of these results was facilitated by the use of FT-NIR spectroscopy. The FT-NIR method also permitted repeated measurements throughout pregnancy to monitor the subject and provide individualized nutritional guidance in the future to maintain a healthy weight gain. The results indicate that the changes in body fat percent and the rate of fat accretion were easily detected during pregnancy, and the suggested actions resulting from this technique, could be based on direct measurements rather than estimates and unreliable methods.

As such, the present invention provides a method to monitor weight gain in a pregnant subject wherein the body fat percentage of the subject is preferably maintained at a constant level during gestation, and the subject's fat accretion rate is monitored so as to preferably follow the fat accretion rate provided by using one or more pre-defined fat accretion determination formulae. By measurement of the body fat percent and fat accretion rates, the weight gain of a subject can be monitored and/or controlled during pregnancy, and thus promote a more healthy weight gain, during pregnancy.

As a result, the present invention provides a major advance in tracking the potential for excessive gestational fat mass accretion, preferably using FT-NIR spectroscopy.

Thus, it is apparent that there has been provided, in accordance with the present invention, a method for measuring and monitoring the fat gain and body fat percent of a subject during pregnancy, which fully satisfies the goals, objects, and advantages set forth hereinbefore. Therefore, having described specific embodiments of the present invention, it will be understood that alternatives, modifications and variations thereof may be suggested to those skilled in the art, and that it is intended that the present specification embrace all such alternatives, modifications and variations as fall within the scope of the appended claims.

Additionally, for clarity and unless otherwise stated, the word "comprise" and variations of the word such as "comprising" and "comprises", when used in the description and claims of the present specification, is not intended to exclude other additives, components, integers or steps. Further, the invention illustratively disclosed herein suitably may be practised in the absence of any element which is not specifically disclosed herein.

Moreover, words such as "substantially" or "essentially", when used with an adjective or adverb is intended to enhance the scope of the particular characteristic; e.g., substantially planar is intended to mean planar, nearly planar and/or exhibiting characteristics associated with a planar element.

Also, while this discussion has addressed prior art known to the inventor, it is not an admission that all art discussed is citable against the present application.

What is claimed is:

1. A method for the measurement and control of body fat percent and body fat accretion during pregnancy comprising:
    measuring the body fat percentage of a mammal at the beginning of said pregnancy using an FT-NIR technique, and monitoring the body fat percentage of said mammal using said FT-NIR technique during the course of said pregnancy;
    measuring the body fat mass of a mammal at the beginning of said pregnancy using weight scales and said measured body fat percentage value, and monitoring the body fat mass of said mammal using said scales and monitored body fat percentage value during the course of said pregnancy;

pre-establishing guidelines, in a calculation device, for the body fat mass gain for a plurality of periods for said pregnancy; and controlling the weight gain of said mammal during said pregnancy to: (i) ensure that the body fat percentage of said mammal remains essentially constant during the course of said pregnancy; and (ii) ensure that the body fat mass gain of said mammal is within the pre-established guidelines for body fat mass gain, for each period of said pregnancy, wherein said mammal is a female human and said pregnancy is broken down into three 13 week trimesters, and the body fat mass gain during each of said trimester is pre-established by guidelines related to each trimester, and wherein said guidelines provide that:

the body fat mass gained during a first trimester is calculated in the calculation device by Formula I, $$Y=\alpha X \quad (I)$$

wherein Y is the fat gain in kg, X is the number of weeks since inception, and $\alpha$ is between 0.08 to 0.16;

the body fat mass gained during a second trimester is calculated in the calculation device by Formula II, $$Y=\beta(X-13) \quad (II)$$

wherein Y and X are as previously defined, and $\beta$ is between 0.25 and 0.42; and the body fat mass gained during a third trimester is calculated in the calculation device by Formula III, $$Y=\gamma(X-26) \quad (III)$$

wherein Y and X are as previously defined, and $\gamma$ is between −0.1 and 0.2.

2. A method as claimed in claim 1 wherein said FT-NIR technique has been calibrated using a calibration model adapted for these applications.

3. A method as claimed in claim 1 wherein the body fat percentage is controlled so that it varies by less than 10% during the course of said pregnancy.

4. A method as claimed in claim 1 wherein said human female is one having a pre-pregnancy weight of between 45 and 100 kg, and having a body fat percent of between 12 to 45%.

5. A method as claimed in claim 4 wherein said human female is one having a pre-pregnancy weight of the woman is between 55 and 75 kg, and the pre-pregnancy body fat percent is between 20 and 35%.

6. A method as claimed in claim 1 wherein $\alpha$ is between 0.12 and 0.14; $\beta$ is between 0.317 and 0.36; and $\gamma$ is between 0.08 and 0.16.

7. An apparatus for measurement and control of body fat percentage and body fat accretion of a human female mammal during pregnancy comprising:

an FT-NIR device which is suitably calibrated using a suitable matrix for measurement of the body fat percentage of said mammal at the beginning of said pregnancy, and throughout said pregnancy;

weight scales for use with said FT-NIR device, for measurement of the body fat mass of said mammal at the beginning of said pregnancy, and throughout said pregnancy;

a database to record the body fat percentage and body fat mass data collected for said mammal during the course of said pregnancy;

a calculation device for determining pre-established guidelines for the body fat percentage and body fat mass during each of three 13 week trimesters of said pregnancy; and notification means to alert said mammal that their diet requires modification, if their body fat percentage is not essentially constant, or if their body fat mass is outside of the pre-established guidelines calculated by the calculation device using Formulae I, II and III:

wherein the body fat mass gained during a first trimester is calculated by Formula I, $$Y=\alpha X \quad (I)$$

wherein Y is the fat gain in kg, X is the number of weeks since inception, and $\alpha$ is between 0.08 to 0.16;

the body fat mass gained during a second trimester is calculated by Formula II, $$Y=\beta(X-13) \quad (II)$$

wherein Y and X are as previously defined, and $\beta$ is between 0.25 and 0.42; and the body fat mass gained during a third trimester is calculated by Formula III, $$Y=\gamma(X-26) \quad (III)$$

wherein Y and X are as previously defined, and $\gamma$ is between −0.1 and 0.2.

* * * * *